(12) United States Patent
Goldberg et al.

(10) Patent No.: US 8,110,812 B2
(45) Date of Patent: Feb. 7, 2012

(54) METHOD AND SYSTEM FOR DETECTING NITROGENOUS MATERIALS VIA GAMMA-RESONANCE ABSORPTION (GRA)

(75) Inventors: Mark Goldberg, Rehovot (IL); David Vartsky, Rehovot (IL)

(73) Assignee: Soreq Nuclear Research Center, Nahal Soreq, Yavne (IL)

( * ) Notice: Subject to any disclaimer, the term of this patent is extended or adjusted under 35 U.S.C. 154(b) by 469 days.

(21) Appl. No.: 12/446,608

(22) PCT Filed: Oct. 24, 2007

(86) PCT No.: PCT/IL2007/001275
§ 371 (c)(1),
(2), (4) Date: Apr. 22, 2009

(87) PCT Pub. No.: WO2008/050327
PCT Pub. Date: May 2, 2008

(65) Prior Publication Data
US 2010/0019165 A1    Jan. 28, 2010

(51) Int. Cl.
*G01J 1/42* (2006.01)
*G01N 23/00* (2006.01)
*G01N 23/04* (2006.01)
(52) U.S. Cl. ............................ 250/395; 250/306; 378/57
(58) Field of Classification Search .................. 250/395, 250/390.04, 390.05, 306, 370.05; 376/159; 378/57
See application file for complete search history.

(56) References Cited

U.S. PATENT DOCUMENTS

| 5,182,764 A | 1/1993 | Peschmann et al. |
| 7,381,962 B2 * | 6/2008 | Goldberg ................. 250/370.09 |
| 7,501,624 B1 * | 3/2009 | Farrell et al. .................. 250/309 |

FOREIGN PATENT DOCUMENTS

WO      2005/059594      6/2005

OTHER PUBLICATIONS

Vartsky David Iet al: "Method for detection of explosives based on nuclear resonance absorption of gamma rays in 14N" Proc SPIE Int Soc Opt Eng; Proceedings of SPIE—The International Society for Optical Engineering 1994 Publ by Society of Photo—Optical Instrumentation Engineers, Bellingham, WA, USA, vol. 2092, Oct. 3, 1993, pp. 307-316, XP002469204.

* cited by examiner

*Primary Examiner* — David Porta
*Assistant Examiner* — Faye Boosalis
(74) *Attorney, Agent, or Firm* — Dekel Patent Ltd; David Klein (57) ABSTRACT

A method for detecting nitrogenous materials within an object by means of Gamma-Resonance Absorption (GRA), including placing on one side of an object a target containing 13C for bombardment with a proton beam of approximately 1.75 MeV energy, to produce a source of 9.172 MeV gamma-rays for scanning the object, reading from the gamma-ray detector the total and the non-resonant attenuations of the incident photon flux, and deriving from the attenuations the net resonant attenuation and the spatial distribution thereof; wherein scanning the object includes: I. performing a rapid pre-scan to classify the overall gamma-ray-attenuation regime and locate regions of high physical density, in which longer scanning times might be required; II. performing a full scan to identify and locate regions that contain nitrogenous materials; and III. performing a plurality of scans in same or different segments to establish presence of explosives.

19 Claims, 6 Drawing Sheets

METHOD AND SYSTEM FOR DETECTING NITROGENOUS MATERIALS VIA GAMMA-RESONANCE ABSORPTION (GRA)

FIELD OF THE INVENTION

The present invention relates generally to the Gamma Resonance Absorption (GRA) imaging method and system for detecting nitrogenous objects, such as explosives in baggage, cargo or vehicles, both in stand-alone mode and in conjunction with other methods, to interdict a broad spectrum of contemporary threats.

BACKGROUND OF THE INVENTION

Gamma Resonance Absorption (GRA) Transmission Imaging is an automatic-decision, non-invasive, non-destructive interrogation method. It detects explosives and distinguishes them from benign objects via spatial reconstruction of the nitrogen density distribution within the inspected item from several radiographic views. GRA is uniquely well-suited to inspection of large, massive items such as air-baggage aggregates, aviation and marine containers, heavy vehicles or railroad cars. One reason is that it combines excellent sensitivity and specificity to nitrogenous explosives with very high radiation penetration, the nitrogen-resonant gamma-ray probe being at 9.172 MeV. Moreover, GRA radiation doses to the environment and screened items are about one order-of-magnitude lower than with any X-ray-based interrogation method, and more than 2 orders of magnitude less than with fast-neutron-based methods.

GRA for explosives detection was first proposed by Soreq NRC to the Federal Aviation Administration (FAA) in 1985 and successfully taken by the inventors through several rounds of experimental feasibility. Notable among the latter are a proof-of-principle laboratory test on individual aviation baggage items (1989), a blind test on aviation baggage aggregates (1993) and a demo run on LD-3 aviation containers (1998). These tests were all conducted at existing accelerator facilities, since the resonant gamma-rays can only be produced with the required spectral quality by 1.746 MeV protons impinging on a $^{13}C$ target.

In the initial stages (1986-93), the R&D on GRA was performed in collaboration with Los Alamos National Laboratory (LANL). The group there evolved a different philosophy to that of Soreq, with respect to: i) employing supplementary gamma-ray lines, ii) the detector of choice (non-resonant-response BGO (bismuth germanate) detectors, as opposed to Soreq's resonant-response nitrogen-rich liquid scintillators) as well as to iii) the inspection methodology (full, multi-view tomography, as opposed to Soreq's plurality of discrete radiographic views). These activities resulted in the following patents being granted to Soreq: IL-86826 (1988)/U.S. Pat. No. 4,941,162(1989)/Europe-89111291.4 (1989); IL-93188 (1990)/U.S. Pat. No. 5,125,015 (1991) and IL-94050 (1990)/U.S. Pat. No. 5,247,177 (1992).

Subsequently, the TRIUMF/Grumman group developed and patented their own version of a non-resonant detector (also employing BGO)—U.S. Pat. No. 5,282,235 (1993), GRA inspection-configuration and chlorine-detection expertise—U.S. Pat. No. 5,784,430 (1996), as well as accelerator target—U.S. Pat. No. 6,215,851 (1998).

Other patents on GRA have been granted to M.I.T, on simultaneous detection of nitrogen and oxygen—U.S. Pat. No. 5,251,240 (1990); Science Research Laboratory of Somerville, Mass., on body-nitrogen assaying—U.S. Pat. No. 5,273,044 (1991) and National Electrostatics Corp. of Middleton, Wis., on a GRA-dedicated accelerator concept—U.S. Pat. No. 5,631,526 (1995). Like the latter, the above-mentioned M.I.T patent also includes claims on beam-recycling.

Finally, several patents on Gamma-Resonance Scattering (GRS) applications, as opposed to GRA transmission-imaging, the topic of the present disclosure, have been granted to Scientific Innovations of Wainscott, N.Y.—U.S. Pat. No. 5,040,200 (1989), U.S. Pat. No. 5,293,414 (1991), U.S. Pat. No. 5,323,004 (1993) and to M.I.T—U.S. Pat. No. 5,115,459 (1990), U.S. Pat. No. 5,420,905 (1993). The latter also include claims on multi-element detection with bremsstrahlung beams. However, the basic properties and figures-of-merit of GRS-applications (particularly, with respect to its spatial imaging capability) differ so radically from those of GRA that the two techniques, although related in terms of their underlying physics, are not on a comparable footing at all.

Gra Method: Fundamental Aspects

Figure 1:
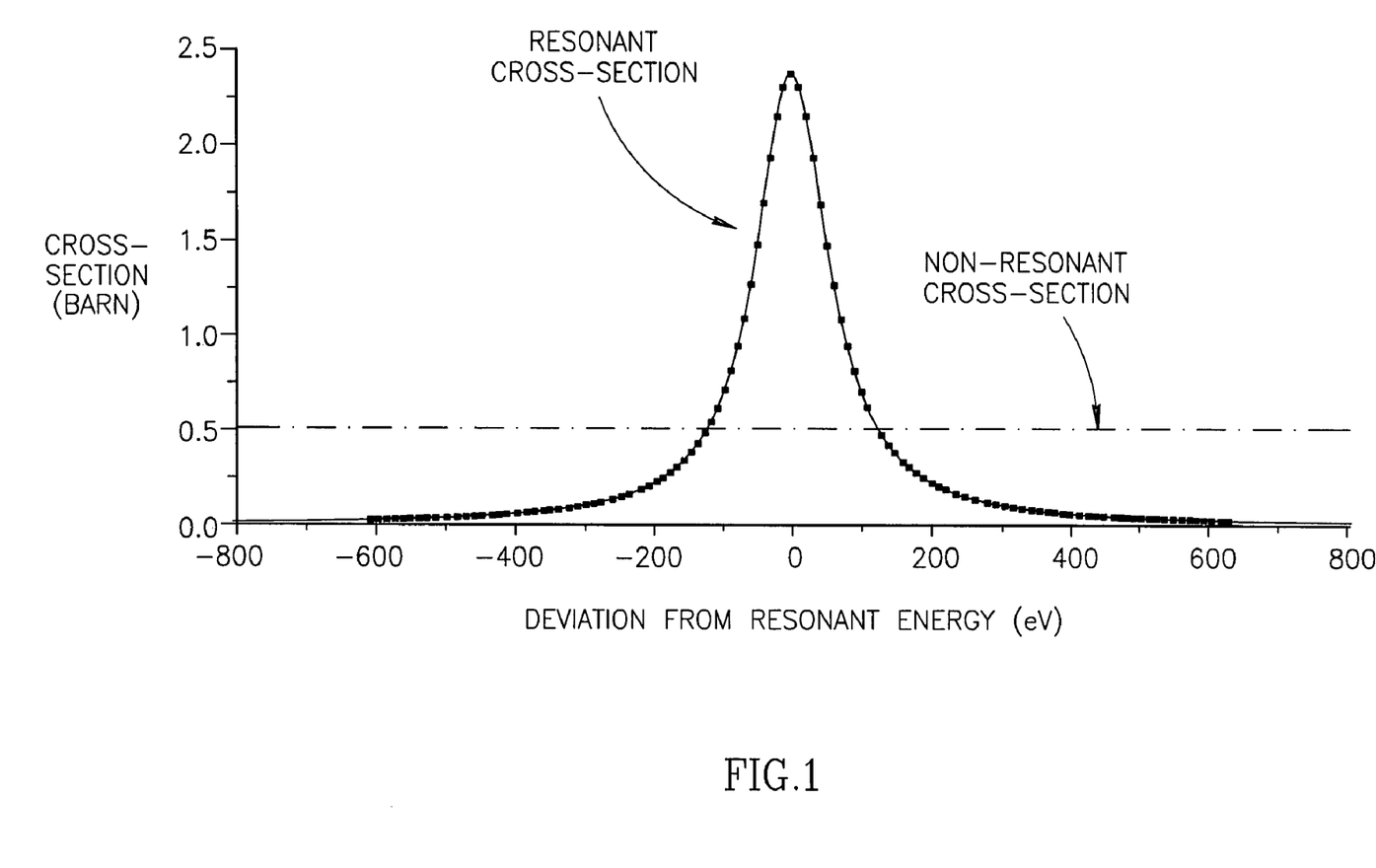
FIG. 1 is a simplified graphical illustration of resonant absorption (squares) and non-resonant (solid line) cross-sections for $^{14}$N at 9.172 MeV.

The resonant absorption cross-section (in the absence of Doppler broadening) for $^{14}N$ nuclei near the 9.172 MeV level is shown in FIG. 1, along with the more familiar non-resonant atomic attenuation processes, primarily Compton scattering and pair production.

In all materials (not just nitrogen) the non-resonant attenuation varies very slowly with gamma-ray energy (by only a few % over a range of ±1 MeV around the $^{14}N$ resonance energy). At precisely the resonance energy (9.172 MeV), the nitrogen resonant absorption cross section is 2.4 barns/atom, which is ~5 times higher than the non-resonant attenuation cross section.

In GRA, the inspected object is scanned by a beam of gamma-rays, a fraction of which represent on-resonance flux at 9.172 MeV, capable of being absorbed by $^{14}N$ nuclei. Thus, the latter will undergo an additional, nuclear resonance component of attenuation that is proportional to the line-integrated areal density of nitrogen in the line-of-sight from source to detector. By measuring the transmitted flux at energies on and off-resonance and normalizing appropriately, both the non-resonant (integral-absorber) and net resonant (total-nitrogen) components of attenuation undergone by the gamma-beam can be extracted.

By taking sets of projected images with an appropriate detector array, one may perform full (multi-view) tomography or take a plurality of discrete radiographic views. Both of these can, in principle, yield the spatial distribution of nitrogen within the interrogated object, with the required precision to distinguish explosives from benign objects.

In summary, the explosives detection capability of GRA stems from its unique combination of high nitrogen specificity and good spatial resolution (by nuclear-based method standards) of typically, 0.1-1.0 cm. The method is potentially attractive for inspecting massive items such as aviation or marine containers, road or rail-based vehicles, by virtue of its 9.172 MeV gamma-ray probe, which is highly penetrating. Moreover, the radiation doses to inspected items or the environment are at least one order of magnitude lower than with any other X-ray, gamma-ray or neutron-based interrogation method.

Source of Resonant Radiation: the $^{13}C(p, \gamma)^{14}N$ Reaction

The ideal gamma-ray source for nitrogen-GRA would be one that emits photons concentrated in an energy interval of the order of the total level width around the 9.172 MeV $^{14}N$ resonance, so that all of them undergo resonant attenuation if the inspected item contains nitrogenous material. In practice, a fundamental difficulty arises from the fact that nuclear recoil losses incurred during emission and subsequent resonant absorption of the gamma-ray by $^{14}$N nuclei are of the order of 2 keV each, much larger than the 128 eV level width. Thus, any radiation emitted from the 9.172 MeV level by nuclei at rest will, of necessity, be far off resonance.

Figure 2:
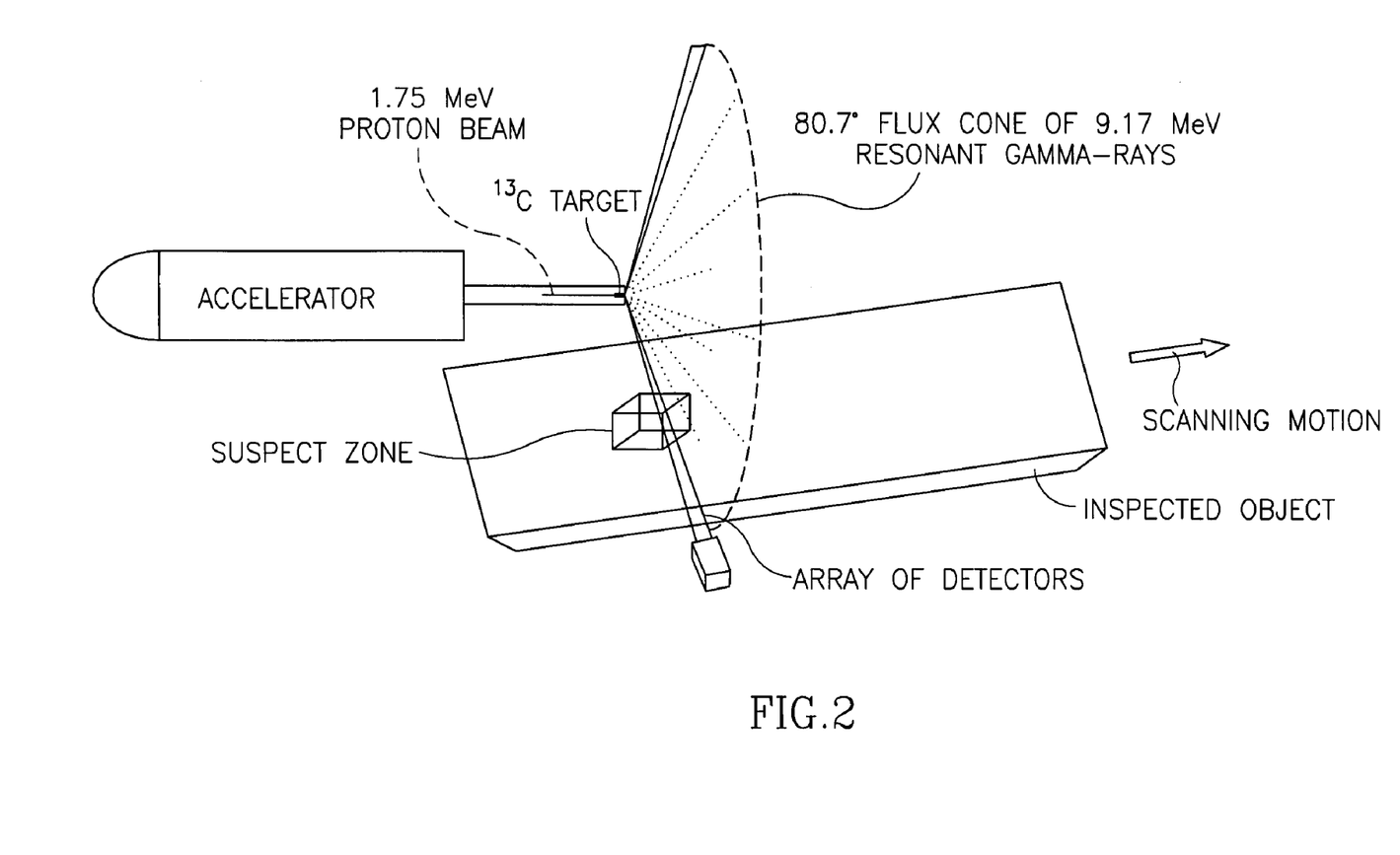
FIG. 2 is a simplified schematic layout of a nitrogen-GRA imaging system, configured around a proton accelerator. Choice of beam direction in space is free, but detectors may only be located on the periphery of the resonant flux cone.

The gamma-ray source closest to the ideal (and in fact, the only practical one for GRA) is the de-excitation spectrum of the $^{14}$N 9.172 MeV level following proton capture via the reaction $^{13}$C(p,$\gamma$)$^{14}$N. This reaction is the inverse of the photo-nuclear resonant reaction $^{14}$N ($\gamma$, p) $^{13}$C. It occurs at a proton energy of 1.746 MeV and the total, thick-target reaction yield into 4$\pi$ is ~6•10$^{-9}$ $\gamma$/proton. As the 9.172 MeV level lifetime (5.1•10$^{-18}$ s) is short compared to ion stopping times (typically ~1•10$^{-12}$ s), gamma-ray emission from excited, recoiling $^{14}$N nuclei occurs in-flight, resulting in the gamma-ray being Doppler-shifted. At a particular polar angle, $\theta_R$=80.7° (with respect to the proton beam), henceforth denoted the resonant angle, the nuclear-recoil losses (during emission and subsequent resonant absorption) are precisely compensated by the Doppler-shifted energy component. Only at the polar angle $\theta_R$, but at all azimuthal angles (forming a resonant flux cone, see FIG. 2) can the 9.172 MeV gamma-rays be resonantly absorbed by $^{14}$N nuclei and serve for nitrogen-GRA. The underlying physics thus dictates the basic spatial configuration for all applications to be as shown in FIG. 2. The choice of proton beam direction at $^{13}$C target is arbitrary; thus, a vertical beam will give rise to an (almost) horizontal flux cone, whereas a horizontal beam will give rise to an (almost) vertical flux cone, around which inspection stations can be built.

The Broadened 9.172 MeV Emission Line and its Principal Implications

All experiments performed over the years (by this and other groups) have consistently shown that, even when employing beams of excellent quality (with respect to proton beam spot-size, divergence and energy resolution) and viewing the resonant flux cone through a narrow slit of 0.25°, the measured FWHM angular aperture required to include most resonant photons is $\Delta\theta_{meas}$~0.75° around the resonant angle $\theta_R$. This value corresponds, via the nuclear reaction and recoil kinematics, to an energy spread of $\Delta E_{meas}$=520 eV, which exceeds the total intrinsic level width by a factor of ~4. Thus, the 9.172 MeV emission line is considerably broadened.

The known contributions that broaden this emission line are as follows:

a) Nuclear level width—128 eV b) Proton beam energy resolution (multiple scattering)—few-eV broadening per keV c) Proton beam optics (parallelism, spot size)—>~120 eV d) Doppler broadening by vibrating target nuclei at elevated target temperatures—40 eV (300° K.), 80 eV (1300° K.)

Clearly, none of the above broadening factors can account for the observed emission line width, even when taken together, unless the proton beam quality (contributions (b) & (c) above) is really poor. Thus, the dominant line-broadening contribution is not yet understood, although it is presumably related to inner-atomic-shell excitation processes in the target atom that occur concomitantly with proton capture by its nucleus. Similar effects have been observed in other light nuclei, when p-capture reactions were employed.

However, in all nitrogen-GRA applications, it is precisely these broadening factors that determine the suitability of a particular radiation source and detector, principally via their effect on nitrogen-image contrast-sensitivity and spatial resolution, as well as resonant yield. In this sense, beam quality specs are closely driven by contributions b), c) above. By the same token, detector-type impacts system performance mainly via its response to resonant and non-resonant radiation.

Figure 3:
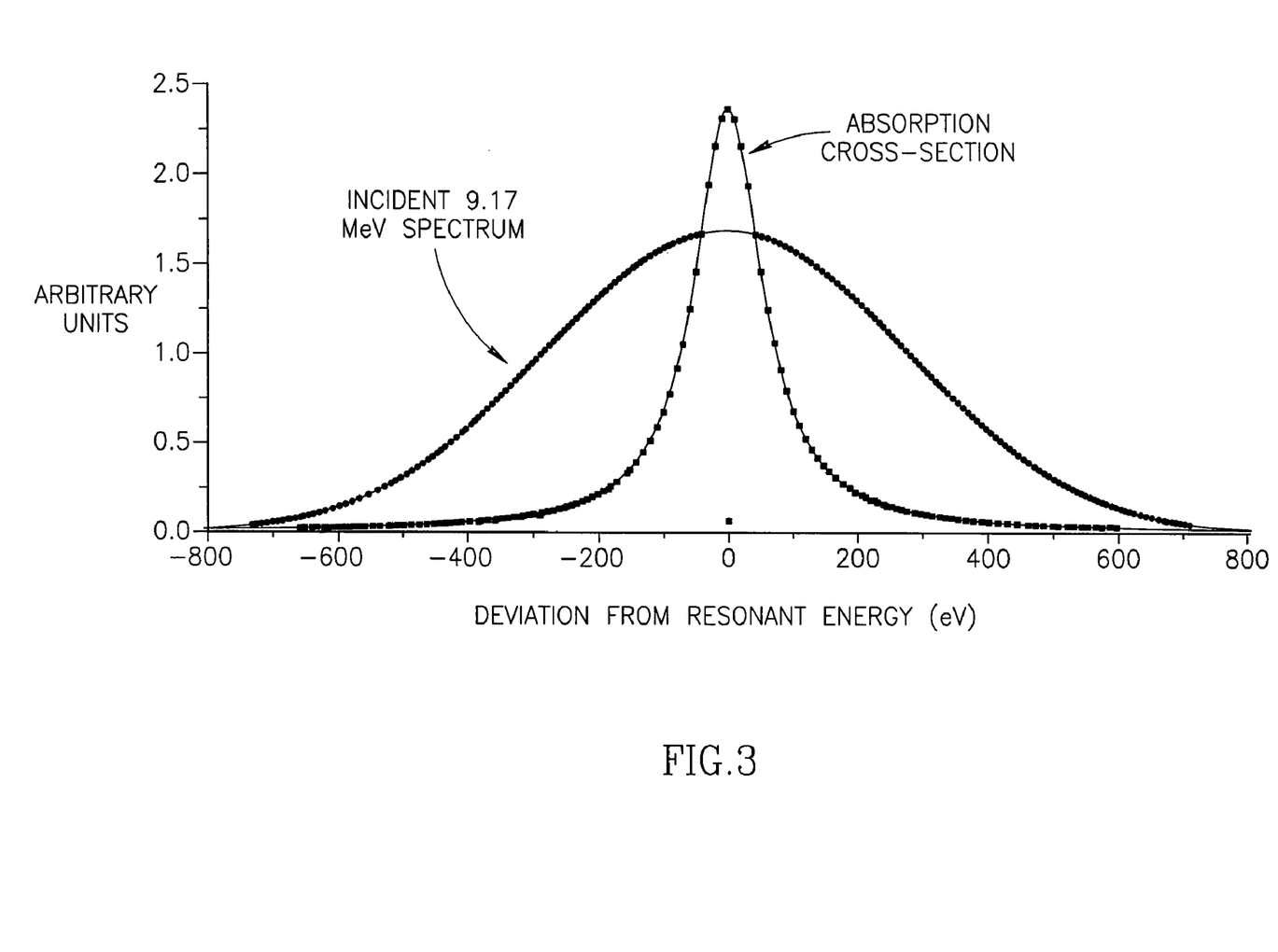
FIG. 3 is a simplified graphical illustration of 9.172 MeV incident spectrum $\Phi(E)$ (circles) and the resonant absorption cross-section (squares).

The shape of the incident 9.172 MeV spectrum is shown in FIG. 3, along with the shape of the absorption cross-section, which is essentially the natural line-width, the Doppler broadening contribution being small. Clearly, the former is much broader than the latter. Consequently, only ~25% of all photons emitted at $\theta_R$ are useful for resonant absorption. The most far-reaching implication of this fact for GRA-system performance is the far-superior nitrogen-image contrast sensitivity obtained with resonant-response detectors than with non-resonant-response detectors.

Detectors

A critical component in all GRA applications is the detector-type used. It has important bearing on the efficiency, contrast sensitivity and susceptibility to scattered radiation. In terms of basic concept, application mode and performance, the latter fall into the following two categories:

a) Non-Resonant-Response Devices (usually, inorganic scintillators)

b) Resonant-Response-Devices (usually, nitrogen-loaded detectors)

a) Non-Resonant-Response Devices: in this category, two versions of BGO detectors have been developed and employed, one by LANL and the other by TRIUMF/Grumman. Both are based on Bismuth Germanate (BGO) detectors that are incapable of distinguishing on-resonance from off-resonance radiation. Consequently, such detectors may suffer from appreciably lower image contrast sensitivity than resonant-response detectors, independent of their operating mode.

b) Resonant-Response Devices: In order to single out the resonant photons from the total radiation transmitted through the inspected object, Soreq has developed nitrogen-rich detectors that are selectively sensitive to photons in the 9.172 MeV±130 eV energy interval. Their resonant-response to radiation stems from the $^{14}$N($\gamma$,p)$^{13}$C photo-nuclear process (the inverse reaction to p-capture on $^{13}$C nuclei) that occurs within the detector medium, exclusively in this energy interval.

In such detectors, resonant events are distinguished from non-resonant ones via the identity of the internally-produced charged particle (protons or leptons). In the proton counting mode, such detectors are inherently insensitive to the non-resonant flux fraction and thus suffer no loss of GRA nitrogen-contrast-sensitivity as a result of the broadened emission line.

In practice, the proton events in an image pixel determine the total attenuation (resonant and non-resonant) undergone by the gamma-ray beam, at that particular line-of-sight from beam/target to detector. The lepton events determine the non-resonant component of attenuation in the same pixel. They are counted in a separate channel.

When the inspected object is scanned, the pixel-by-pixel lepton count distribution forms the non-resonant (integral-absorber) image ("Gammagram"), which is a conventional transmission radiogram at 9.172 MeV. The corresponding pixel-by-pixel ratios of proton to lepton count form the net-resonant (total nitrogen) image ("Nitrogram").

In the Nitrogram, all non-nitrogenous items are rendered completely transparent, if the pixel information is appropriately normalized. This is rigorously the case if resonant-response detectors and single-line 9.172 MeV spectra are employed, since the Nitrogram and Gammagram are obtained simultaneously in strictly identical geometry at the resonant angle $\theta_R$ and at the same photon energy (to within $<\sim 1$ keV). With such artifact-free data (see also the embodiment below of "Correcting for Proton-Beam- & $^{13}$C-Target-Related Data Artifacts"), taking a plurality of discrete radiographic views enables reconstruction of the nitrogen-density distribution within the inspected object to a precision that is adequate for low-level explosives detection.

However, this pixel normalization requirement is not rigorously fulfilled if: a) lines other than 9.172 MeV are present in the gamma-ray beam, or if: b) the Gammagram is determined at an angle adjacent, but not identical to $\theta_R$. In both these cases, Nitrogram artifacts are produced and image clutter increases markedly. This is prohibitive for the approach of taking a plurality of discrete radiographic views advocated here—the sole realistic option for inspecting massive cargo containers and heavy vehicles—as it effectively prevents determining the nitrogen density distribution within the inspected object to the precision required.

Thus, the two preceding paragraphs respectively define sufficient and necessary conditions for taking a plurality of discrete radiographic views with GRA, for low-level explosives detection applications.

SUMMARY OF THE INVENTION

The present invention seeks to provide improved methods and systems for detecting nitrogenous materials and determining their nitrogen-density distribution within an object by means of Gamma-Resonance Absorption (GRA), in particular nitrogen-GRA. The invention includes, without limitation: Multi-Level Inspection-Methodology; Resonant-Response & High-Spatial-Resolution Detectors; Correcting for Proton-Beam- & $^{13}$C-Target-Related Data Artifacts; Use of Ultra-High-Energy-Resolution Proton Beams; as well as Combining GRA with Other Inspection Systems.

BRIEF DESCRIPTION OF DRAWINGS

The present invention will be understood and appreciated more fully from the following detailed description taken in conjunction with the drawings in which.

DESCRIPTION OF EMBODIMENTS

The improvements in GRA system performance due to the above pertain to nitrogen-image contrast, spatial resolution, image noise, as well as the elimination of normalization artifacts due to accelerator-beam instabilities and(or) $^{13}$C-target-degradation effects. These improvements translate to enhanced system performance characteristics for inspected-object handling logistics and throughput, threat object detection, as well as reduced false-alarm rates.

Some embodiments of the invention provide stand-alone GRA explosives detection systems that are truly of multi-level nature. In practical terms, this means that the screening sequence undergone by each inspected item is flexible, automatically-controlled and optimally-geared to clarifying its threat status with the highest achievable confidence level and within the minimal screening time.

In this context it is noteworthy that, for multi-level screening of large cargo items, such as containers, trucks and rolling stock, the plurality of discrete radiographic views variant of GRA disclosed herein is the only practicable option since, as described above, full, multi-view tomography is prohibitive for such items.

Some embodiments of the invention provide enhanced detection of threat objects, primarily via improved spatial resolution. Thereby, they also tend to reduce the false alarm rates.

Some embodiments of the invention employ liquid-capillary array or solid-fiber-bundle scintillators in fast-neutron and gamma-ray spectrometry-cum-imaging methods and systems that operate in mixed gamma-ray and neutron radiation fields.

Some embodiments of the invention provide for real-time corrections to the pixel data due to accelerator beam instability or target degradation effects. Thereby, they tend to improve GRA image quality, by reducing normalization artifacts.

Some embodiments of the invention provide for enhanced GRA spatial resolution and detection efficiency by employing ultra-high energy-resolution proton beams.

Some embodiments of the invention provide for operation of a GRA inspection system in conjunction with other technologies/systems (a number of which may share a common particle accelerator), to enhance throughput and to address a broader spectrum of threat materials.

1. Multi-Level Inspection-Methodology

Even with mA-intensity proton beams, the resonant 9.172 MeV gamma-ray yield of the $^{13}$C(p,$\gamma$) reaction at the 1.746 MeV capture resonance is relatively low. Thus, the interrogating radiation needs to be judiciously utilized, if a GRA system is to achieve high throughput and high detection probability for small quantities of explosives with few false-alarms.

As outlined in the GRA METHOD—FUNDAMENTAL ASPECTS section and illustrated in FIG. 2, GRA imaging may be performed with arrays of detectors on the periphery of the $\theta_R$=80.7° resonant flux cone.

Furthermore, this flux cone can be divided into angular segments, in which (see FIG. 2) a plurality of GRA inspection stations can be constructed. This opens up a number of attractive options that can exert a major bearing on the methodology of GRA inspection and the performance of operational systems based thereupon. Specifically, the latter refer to the following:

a) enhanced throughput (more efficient use of the available resonant radiation)

b) parallel processing (what transpires in one segment is independent of the others)

c) generating several, discrete radiographic views in the same, or in different segments d) multi-level screening (via flexible, automatically-controlled inspection sequences)

In this section, we will primarily deal with options (c) & (d).

Figure 6:
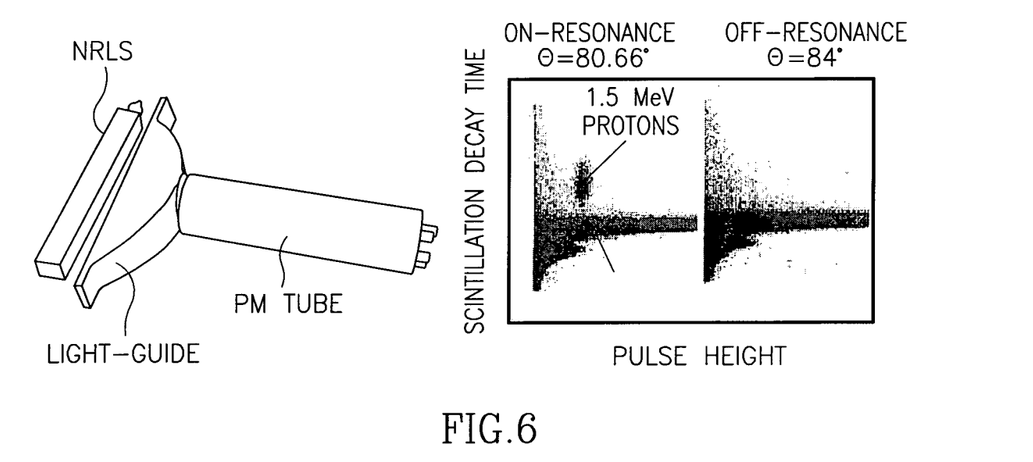
FIG. 6 is a simplified illustration of detector components (left) and typical two-dimensional spectra obtained with it, on and off resonance.
Figure 7:
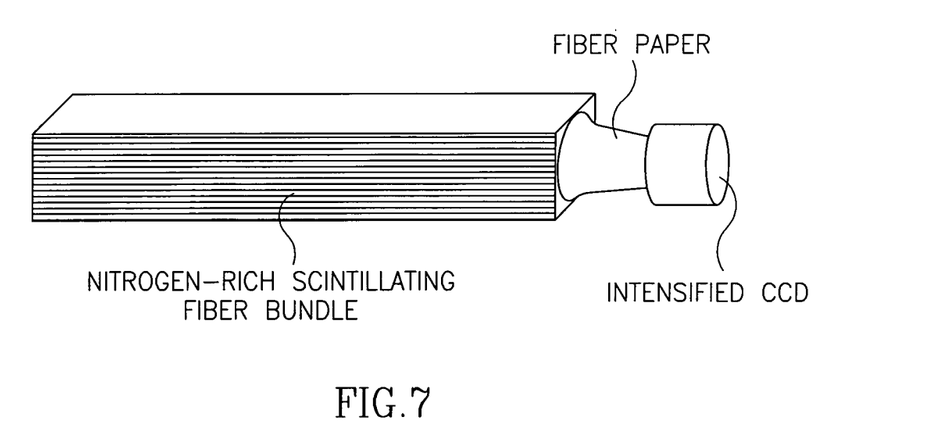
FIG. 7 is a simplified schematic illustration of a typical liquid capillary array or solid-fiber-bundle detector.

A non-limiting embodiment of a GRA system that screens palletized cargo, containers, trucks and other massive objects by taking a plurality of discrete radiographic views is illustrated in FIGS. 6 and 7. The typical inspection sequence for such an object may include one or more (in most cases, not more than two) of the following stages:

I. a rapid pre-scan, to classify the overall gamma-ray-attenuation regime and locate regions of high physical density, in which longer scanning times might be required II. a full scan (one view), to identify and locate regions that contain nitrogenous materials III. several scans (views) in same or different segments, to establish presence of explosives IV. localized (possibly slow) scans of specific regions, to confirm presence of explosives V. repeat of any of the above in borderline cases, to reduce false-alarms As evident from the above text and figures, without limitation, a flexible-inspection-sequence GRA facility may function as follows:

The default mode of operation may include, but is not limited to, two parallel screening systems (on the upper and lower planes of FIG. 6), each generating two views of screened objects, the minimum required to spatially-reconstruct nitrogen-density distributions.

In case of an alarm, the inspected item might be shunted onto the other plane, to generate several more independent views, which could resolve the nature of the alarm. In this case, parallel processing on the latter plane would be temporarily halted.

When very massive cargo items are inspected, it might prove advantageous to modify the default screening mode in advance. For instance, one might choose to devote one of the angular segments of the resonant flux cone (not necessarily 4 quadrants) to fast pre-scans and to use the other segments for generating high-statistics radiographic views.

Should the alarm persist, the issue might be resolved by performing one or more repeat scans, possibly at a slower transport velocity, to enhance image statistics.

The above serves to illustrate, without limiting, the flexible sequence associated with such a GRA configuration. Automatic-decision systems constructed in accordance with the invention can thus serve both as $1^{st}$ and $2^{nd}$-levels within a multi-level facility. Some advantages include high explosives detection capability and low-false-alarm rates at maximal throughput.

In the GRA system of the present invention, it is feasible to place all decision-making under computer control, with respect to: the specific scanning sequence to be performed, the mechanical motions required to execute it, as well as the data acquisition modes and analysis routines implemented for appraising the status of the inspected item ("as yet undetermined", "clean", "suspect" or "bingo") throughout its interrogation.

2. Resonant-Response & High-Spatial-Resolution Detectors

The configurations and operating modes for two principal, resonant-response variants of a nitrogen-rich, detector are presented. These can be categorized as:

2.1) Bulk Organic Scintillators (Liquid & Solid)

2.2) High-Spatial-Resolution, Liquid-Capillary or Solid-Fiber Scintillator Arrays These variants differ from each other primarily in the manner whereby the internally-produced ~1.5 MeV protons indicative of a resonant interaction (the associated ~120 keV $^{13}$C ions contribute very little to the detection process) are distinguished from Compton electrons and electron-positron pairs that result from non-resonant interactions.

2.1) Bulk Organic Scintillators 2.1.1) Nitrogen-Rich Liquids

Figure 4:
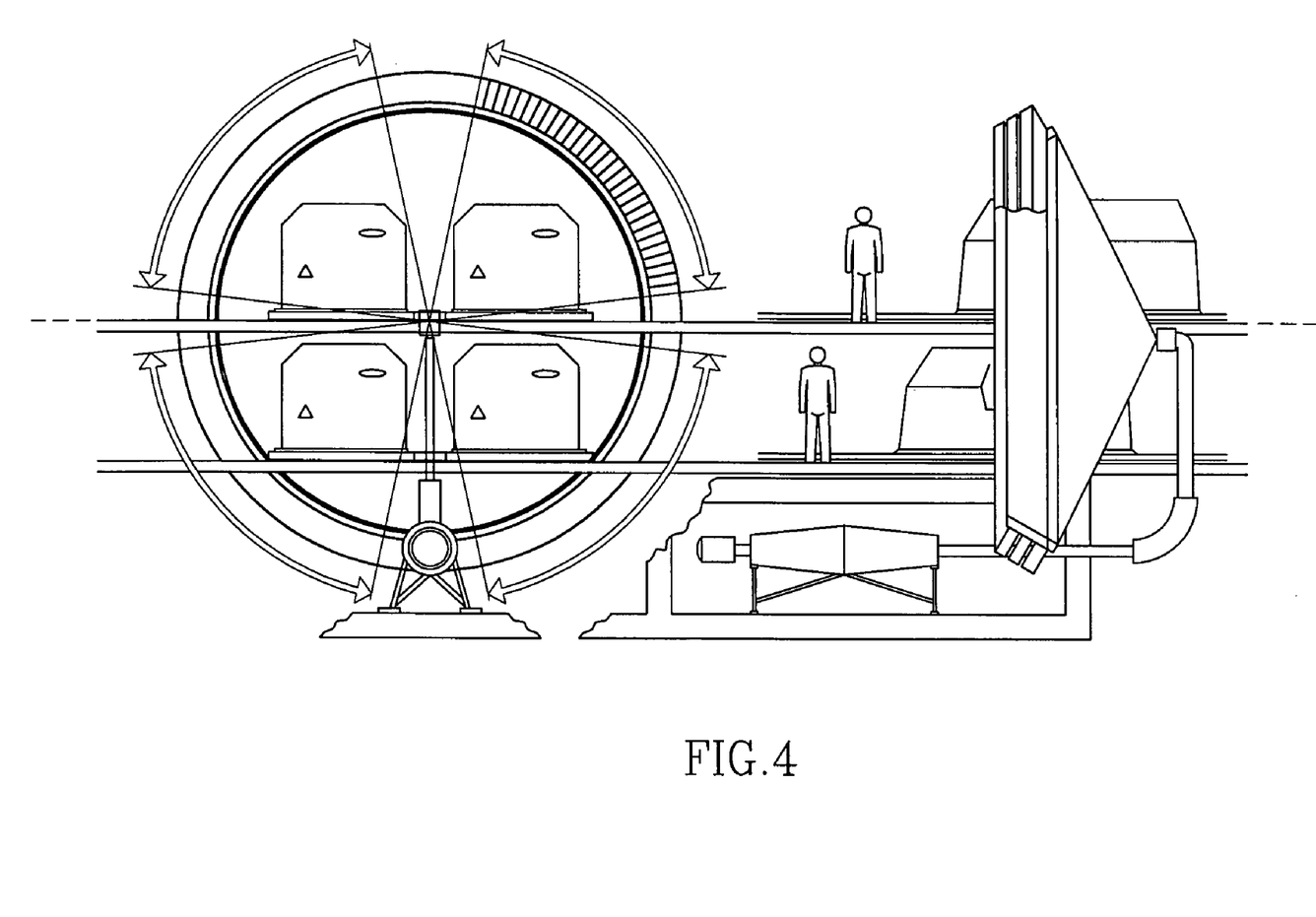
FIG. 4 is a simplified illustration of face-on (left) and side-on (right) vertical cross-sections through an GRA inspection system, in accordance with an embodiment of the present invention, showing how independent views are obtained of an object presented in identical orientation to different angular segments (not necessarily four quadrants, as shown) of the system. Accelerator, beam transport system and target location are shown. The choice of beam direction on target (which dictates the orientation of the resonant flux cone) is free, but detectors are located on the resonant flux cone periphery.

FIG. 4 shows an exploded-view photograph of one such detector, a nitrogen-rich liquid scintillator (NRLS) possessing pulse-shape-discrimination (PSD) properties, along with the two-dimensional (scintillation decay-time vs. pulse-height) 9.172 MeV spectra registered with it on and off the resonant angle. The fundamental concept underlying this detector was already presented in U.S. Pat. No. 4,941,162 and associated IL, European Patents (see background of the invention), but its realization and experimental performance are disclosed here for the first time, along with the rationale for employing this device as the detector of choice in most GRA applications (see also previous sections).

In these detectors, the internally-produced 1.5 MeV proton events are detected with 100% efficiency and can be distinguished via Pulse Shape Discrimination (PSD) from the numerous electrons and positrons (leptons) produced by gamma-rays that do not interact resonantly. PSD is based on the difference in scintillation decay times for high ionization (proton) and low ionization (lepton) events, which can be translated by an appropriate analog or digital electronic circuit to time peaks separated by, typically, 10-20 ns. Counting the proton signal provides a measure of the total transmission attenuation (resonant and non-resonant). In a simultaneous measurement, the non-resonant attenuation is determined by counting the integral lepton signal.

In a non-limiting embodiment, the detector enclosure may be a parallelepiped-shaped vessel, typically 20×20×240 mm$^3$ in dimensions, with at least one glass side for viewing the scintillation light. The vessel may be coupled via a parabolic Perspex light-guide to a 50.8 mm PM tube, the entire assembly being enclosed by a light-tight cover. The 20×20 mm$^2$ detector face is presented normal to the γ-ray beam, forming a pixel of these dimensions, the long (240 mm) dimension being in the efficiency direction (extending radially along $\theta_R$).

FIG. 4 (right) shows that the 1.5 MeV proton events created in the $^{14}$N(γ,p)$^{13}$C reaction by resonant photons are well separated from the continuum of leptons created by all photons in the incident spectrum. By electronically selecting a two-dimensional region of interest around the proton peak, one can count the proton events only, with a signal-to-background ratio (for proton to lepton events) exceeding, typically 15:1.

2.1.2) Nitrogen-Rich Solids

It is well known that certain solid organic ("plastic") scintillators do exhibit PSD properties, albeit to a lesser extent than the optimal liquids developed for this purpose. However, in terms of mass-production, robustness and ease of packaging, the solid versions have clear advantages over their liquid counterparts, particular where multi-detector arrays are required, as in large-cargo inspection systems based on nitrogen-GRA. The overall detector configuration may be similar, but is not limited to, that of the liquid detector described above.

2.2) High-Spatial-Resolution, Liquid-Capillary or Solid-Fiber Scintillator Arrays 2.2.1 GRA Detectors As mentioned above, typical transverse dimensions of organic scintillators for nitrogen-GRA imaging applications correspond to subtended apertures $\theta$, $\phi < \sim 0.75°$ (polar and azimuthal angles). Their typical lengths (in the efficiency direction) are 10-30 cm. With such detectors, proton/lepton (or resonant/non-resonant gamma-ray) event discrimination can only be effected via the intrinsic detector properties, such as PSD.

However, an alternative particle identification method can be implemented if the transverse dimensions of a basic scintillator cell are reduced to capillary or fiber size (~50 μm), comparable to 1.5 MeV proton ranges, but appreciably smaller than typical tracks of energetic leptons.

Figure 5:
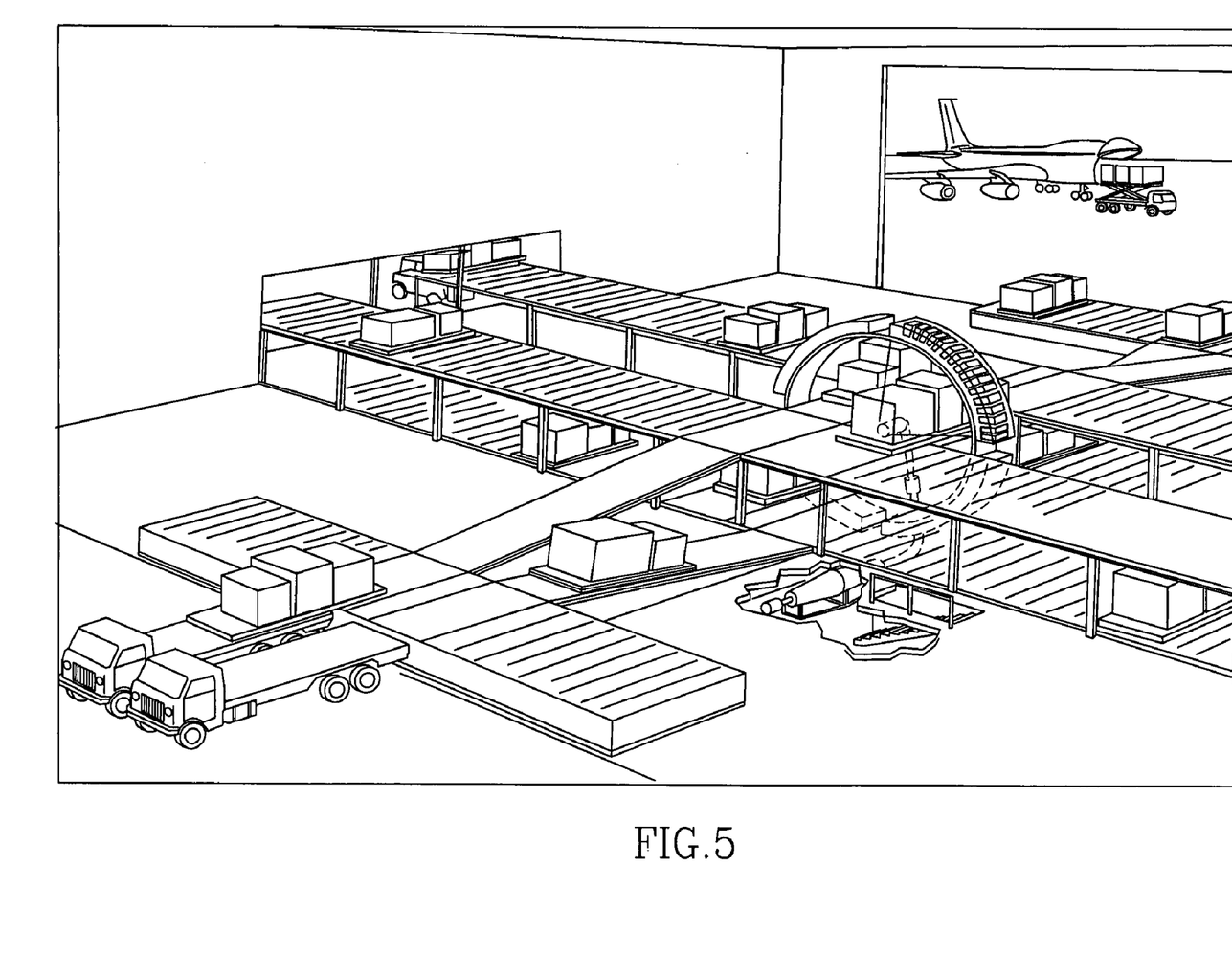
FIG. 5 is a simplified pictorial illustration of an operational GRA cargo inspection facility, with flexible inspection sequence capability, in accordance with an embodiment of the present invention. As previously mentioned, the choice of beam direction on target (which dictates the orientation of the resonant flux cone) is free, but detectors may only be located on the resonant flux cone periphery.

In such a case, a detector unit of the above type is built up as a 2-dimensional aggregate of such basic cells, each acting as a fiber light-guide for scintillation light, as illustrated in FIG. 5.

Here too, nitrogen-rich scintillating cocktails must be employed but, in contrast to section 2.1 above, PSD capability is no longer required in this case. Using optical methods, proton/lepton discrimination can be effected on an event-by-event basis by imaging (in the two available dimensions) projected track lengths of individual events and scintillation yield per unit track length. For example, at capillary or fiber diameters of ~50 μm, a resonantly-produced 1.5 MeV photoproton will create a strong light signal either in a single cell, or in a maximum of two adjacent neighboring cells. In contrast, lepton events will have considerably longer tracks and will generate significantly less light/pixel.

Thus, a two-dimensional analysis (track-length vs. light/pixel) will permit reliable proton/lepton event discrimination with sub-mm resolution.

This can be done using optical techniques, such as, but not limited to, CCD readout following image intensification. Since overall GRA count rates are not high (typically, $10^1$-$10^3$ cm$^{-2}$·s$^{-1}$), track densities after exposure times in the 1-100 ms range will be low enough to permit reliable assignments of particle type and position to each event registered.

Using such detectors will permit GRA inspection of objects with sub-mm spatial resolution, with all the associated imaging advantages that this entails.

2.2.2 Other Detectors Based on Similar Principles, such as a High-Spatial-Resolution Fast-Neutron Spectrometer Distinguishing different types of events (particles) on the basis of track length and amount of scintillation light is a potent tool in numerous other imaging methods, such as (but not limited to) those involving mixed gamma/fast-neutron radiation fields. Methods of this type include, but are not limited to: Fast-Neutron Radiography (FNR) and Fast-Neutron Resonant Radiography (FNRR), with either broad-spectrum or mono-energetic neutron beams, of which Pulsed Fast-Neutron Transmission Spectrometry (PFNTS) is a pulsed-beam version.

In applications of these methods, the detector needs to contain appreciable amounts of hydrogen, does not have to be nitrogen-rich and may possess the following properties:

1) good gamma/neutron event discrimination
2) neutron spectrometry capability
3) sub-mm spatial imaging resolution Liquid-capillary-array or solid-fiber-bundle scintillator detectors coupled to an optical imaging device, such as a CCD camera, are eminently appropriate for these applications. In such detectors, the neutron is detected by measuring the scintillation light yield and the track length of a resulting recoil proton. Thus (as in the GRA detector, see section 2.2.1 above) a two-parameter analysis (track length projection and total light yield) will permit reliable proton/lepton event discrimination, along with sub-mm position resolution.

Moreover, in all neutron radiography techniques, the direction of the neutrons incident on the detector is known. Thus the incident neutron energy can be determined from the scintillation light yield due to the resulting recoil proton and the projection of its track, using a readout system and data analysis procedure similar to that described above in section 2.2.1.

Furthermore, integral acquisition mode will, in many cases, render the data readout and handling system considerably simpler and more cost-effective.

At present, FNR & PFNTS utilize several variants of time-of-flight spectrometry, in order to obtain gamma/neutron discrimination combined with high neutron energy resolution. Such methods necessarily: a) rely on neutron beam bursts that are, typically, 1-2 nanoseconds broad (which can only be produced with complex, pulsed accelerators), and b) involve relatively long flight-paths from neutron-source to detector (typically, 5-15 meters). On both these counts, the useful neutron flux intensity is quite severely limited and the experimental infrastructure cumbersome and costly.

The present invention will also permit, but is not limited to, operation with a CW neutron source and furthermore, will be practicable at considerably shorter neutron-source/detector distances (typically 1-3 meters) than is presently the case. Operationally, this is of crucial importance, particularly when working in intense radiation fields.

3. Correcting for Proton-Beam- & $^{13}$C-Target-Related Data Artifacts

In this section we present a novel method for improving GRA image quality and thereby also system performance. It pertains to: a) improving data normalization to the instantaneous resonant flux and b) data feedback to correct longer-term proton-beam drifts.

The intensity, emission-line width and energy-centroid of the 9.172 MeV photon beam emitted from the $^{13}$C(p,γ)$^{14}$N reaction may fluctuate during data accumulation due to accelerator-beam-instabilities or $^{13}$C-target-degradation effects. In previous work only the overall intensity of the gamma-ray beam was monitored using a non-resonant detector, such as NaI or BGO. In the present invention we monitor both the intensity and the spectral quality of emitted 9.172 MeV gamma-rays.

a) As shown in FIG. 3, the 9.172 MeV emission line is broader than the resonant absorption line. Consequently, only a fraction of the incident 9.172 MeV photons will undergo resonant interactions (in addition to the electronic interactions) in the inspected object or in the resonant detector. This resonant fraction depends on the spectral beam quality. The present invention monitors the beam quality by measuring the resonant fraction of the incident photon spectrum in real time.

The instantaneous correction for the above fluctuations can be effected during the scan by introducing a resonant flux monitor, in addition to the above-mentioned non-resonant monitor. Such a resonant monitor must be independent of the flux attenuations caused by the inspected object; thus, it can be positioned either as a transmission detector close to the accelerator target or as a regularly-configured imaging detector at the extremities of the array (that are unobscured by the object).

Measuring the instantaneous ratio of the detected proton-to-lepton count ratio in the monitor and using the latter to normalize the imaging array data will significantly improve GRA image quality.

b) when fed back to the accelerator control system, the outputs of the resonant flux monitor can also provide data for automatic correction of beam energy, to correct for drifts in accelerator parameters due to power supply instabilities. In the case of electrostatic accelerators, this can usually be effected by an appropriate change in the terminal corona discharge, which affects the overall machine voltage. For RF-based accelerators, the desired change can usually be obtained by a minor modification to the RF gradient, or to its phase.

4. Ultra-High Energy-Resolution Proton Beams

As mentioned above, emission-line broadening has far-reaching implications for the methodology and performance of components and systems. Among others, as also mentioned above, it severely reduces the nitrogen contrast-sensitivity achievable with non-resonant-response detectors, which tips the scales heavily in favor of resonant-response devices.

However, under specific conditions, it may prove possible to realize a nitrogen-GRA system in which such broadening effects are markedly reduced. This assertion relates to the plausible assumption that line-broadening stems from inner-atomic-shell excitation processes in the $^{13}$C target atom, which occur concomitantly with p-capture by its nucleus.

Such simultaneous atomic+nuclear reaction effects are kinematically allowed on condition that the beam projectile velocity (here, $v_p$~0.061 c) is comparable to the Bohr velocity of K-shell electrons in the compound $^{13}$C+p atom ($v_B$=Z/α~0.051 c), Z=7 being the atomic number and α=$\frac{1}{137}$ the fine structure constant. Clearly, this condition is well fulfilled. Indeed, detailed micro-structure studies of resonant-yield excitation functions with ultra-high E-resolution particle beams have revealed that effects of this type do occur.

Thus, using a 1.746 MeV proton beam with ultra-high energy-resolution and stability of, typically, ~100 eV or better (well below the K-shell electron binding energy in the $^{13}$C target atom), the target can be bombarded at a mean energy on the low-E flank of the p-capture resonance excitation curve, such that the purely-nuclear reaction process is energetically allowed, but the simultaneous nuclear-atomic excitation process is forbidden, as it requires a supplementary energy of ~400 eV that the protons do not possess.

This approach is likely to incur the expense of reduced resonant yield. Nevertheless, if thereby, the width of the emission-line is restored to values close to the total 9.172 MeV level width of 128 eV, the 80.7° resonant flux cone will become markedly narrower, and the spatial resolution of the GRA imaging system will correspondingly improve. This could be of, but is not limited to, critical importance in scenarios where detecting thin-sheet explosives is a high priority.

Moreover, another major advantage would be gained, which is likely to offset the loss in resonant yield. This relates to the fact that, if the emission line is not appreciably broader than the natural level width, there is nothing to be gained (in contrast sensitivity) by using resonant-response detectors. In such a case, non-resonant response detectors, which exhibit considerably higher efficiency to 9.172 MeV γ-rays, would work just as well, or better.

5. Combining GRA with other Inspection Systems

Depending on the detailed inspection scenario and nature of threat-objects to be detected, it may be of interest to deploy the GRA screener described here as part of a multi-tiered explosives-detection facility, in conjunction with another inspection system or systems.

a) The latter could be, but are not limited to, a Bremsstrahlung-based, single or dual-energy radiography or tomography system, or even a fast-neutron-based imaging system such as FNRR (see above), possessing favorable explosives detection capabilities. Any of these may function as a $1^{st}$-tier inspection device, the GRA screener of the present invention being used as a $2^{nd}$-tier system, primarily to resolve false alarms generated by the $1^{st}$-tier system. In such cases, it may be possible to reduce the 1.746 MeV proton beam intensity required from the GRA-dedicated accelerator to sub-mA values, which would render the machine simpler and appreciably less costly. Combined systems of this type might exhibit considerably enhanced throughput and detection performance characteristics than either of them separately.

b) Alternatively, the explosives detector of the present invention could serve as a $2^{nd}$-tier scanner, behind another system such as, but not limited to, a dual-E radiographic detection system for special nuclear materials (SNM). Since the latter may also possess explosives detection capabilities, by virtue of its ability to localize regions of dense, low-Z material, deploying such systems in a multi-tiered hierarchy could prove of interest when operational requirements call for detecting explosives, SNM and (or) other threat objects in a single inspection sequence.

c) A further possibility would be to operate the GRA screener of the present invention in series or in parallel with some other threat-material detection device or devices, without a defined hierarchy and inspection sequence among the deployed systems being established in advance. Such combinations will, in general, not reduce overall footprint and cost, but may provide the user with added flexibility and sensitivity in countering specific, time-varying threat scenarios.

d) Finally, an embodiment of a dedicated ion accelerator that could be shared by GRA and another nuclear-reaction-based dual-E radiography system is disclosed. It pertains to a machine capable of accelerating mixed (or alternately-produced) d$^+$ and H$_2^+$ beams of intensities in the 0.5-5.0 mA range, at precisely twice the energy of the 1.746 MeV $^{13}$C(p,γ) capture resonance. The implications of this disclosure are discussed below.

Option (d) may provide a solution for applications that call for detection of high-Z materials and nitrogenous explosives in a single system, or even in the very same scan. In the latter case and in accordance with this disclosure, one could bombard a thin $^{13}$C layer deposited on the surface of a thick $^{11}$B target, with a mixed mass=2 beam of H$_2^+$ (majority ion) and d$^+$ (minority ion). The H$_2^+$ molecular ions, when they impinge on the $^{13}$C layer, will break up (via the so-called Coulomb explosion process) into two almost parallel, equal-energy protons at the 1.746 MeV resonance, as required for a GRA screener. The emission-line broadening contribution due to the Coulomb explosion is not expected to prove excessively large for GRA applications. After traversing the $^{13}$C layer, the protons will enter the $^{11}$B target, where they will contribute to high-energy gamma-ray production via the p-capture reaction. The deuteron component will traverse the $^{13}$C layer (which will contribute little in the way of reaction yield, the $^{13}$C being thin) and interact with the $^{11}$B target via the (d,n) reaction described in IL Patent Application No. 159406 (filed Dec. 16, 2003) and PCT application Ser. No. 10/582,763 (filed Dec. 14, 2004).

Alternatively, should it be of interest to configure the high-Z and explosives detection systems around the same accelerator without performing the scans simultaneously, a simpler variant of the above is feasible: one could accelerate mass 2 to the required energy of around 3.5 MeV in the machine, switching between molecular hydrogen and atomic deuterium ions in the ion source (and also changing the respective target) as required by the nature of the application at any given moment.

Any of these options could enhance system performance characteristics (in terms of addressing a broader spectrum of threat objects), as well as improving cost-effectiveness, by sharing a dual-purpose accelerator.

In cases where the present GRA screener is operated in conjunction with other nuclear-reaction-based inspection systems, as described hereinabove, it is clear that other considerations may also have a bearing on accelerator specifications, design and performance. These will have to be taken into account in designing a multi-level or multi-purpose security inspection facility.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. A method for detecting nitrogenous materials within an object by means of Gamma-Resonance Absorption (GRA), comprising:
   (i) placing a target on one side of an inspected object, said target containing $^{13}C$ for bombardment with a proton beam of approximately 1.75 MeV energy, to produce a source of 9.172 MeV gamma-rays;
   (ii) placing on an opposite side of the object, on the periphery of a flux cone at polar angle $\theta_R=80.7°$ with respect to the proton beam, a gamma-ray detector with a nitrogen rich detection medium;
   (iii) screening the object with a gamma-ray beam from said source;
   (iv) reading from said gamma-ray detector total and non-resonant attenuations of incident photon flux;
   (v) deriving from said attenuations a net resonant attenuation and spatial distribution thereof; and
   (vi) determining a status of said inspected object based on a nitrogen-density distribution derived from said net resonant attenuation and said spatial distribution thereof;
   wherein screening the object comprises one or more of the following steps:
   I performing a rapid pre-scan to classify an overall gamma-ray-attenuation regime and locate regions of high physical density;
   II performing a full scan to identify and locate regions that contain nitrogenous materials;
   III dividing said flux cone into azimuthal angular segments and performing a plurality of scans in at least some of said segments to establish presence of explosives; and
   IV performing localized scans of specific regions to confirm presence of explosives.

2. The method according to claim 1, further comprising repeating any of steps I-IV, as required to determine said status of said inspected object.

3. The method according to claim 1, further comprising generating a plurality of discrete radiographic views in the same segments.

4. The method according to claim 1, further comprising generating a plurality of discrete radiographic views in different segments.

5. The method according to claim 1, wherein said gamma-ray detector comprises a nitrogen-rich liquid scintillator (NRLS) that distinguishes between on-resonance and off-resonance events via Pulse-Shape-Discrimination (PSD).

6. The method according to claim 1, wherein said gamma-ray detector comprises a nitrogen-rich solid organic ("plastic") scintillator that distinguishes between on-resonance and off-resonance events via Pulse-Shape-Discrimination (PSD).

7. The method according to claim 1, wherein said gamma-ray detector comprises a scintillator whose basic cell transverse dimensions are comparable to proton ranges from on-resonance events and considerably smaller than lepton ranges from off-resonance events.

8. The method according to claim 1, wherein said gamma-ray detector comprises a scintillator whose basic cell transverse dimensions are ~50 μm.

9. The method according to claim 1, wherein said gamma-ray detector comprises a scintillator whose basic cells act as fiber light-guides for scintillation light, and wherein proton/lepton discrimination is effected by imaging track lengths of individual events and scintillation yield per unit track length.

10. The method according to claim 9, further comprising performing proton/lepton event discrimination via at least one of a single-event-counting technique, an integrative technique and an optical technique.

11. The method according to claim 1, wherein screening the object with the gamma-ray beam comprises performing GRA imaging with sub-mm spatial resolution.

12. The method according to claim 1, further comprising measuring resonant fraction of the incident photon flux in real time with a resonant flux monitor and using outputs of said resonant flux monitor to adjust operational parameters associated with screening the object.

13. The method according to claim 12, further comprising measuring an instantaneous ratio of a detected proton-to-lepton count ratio in said resonant flux monitor and, using said ratio to normalize imaging array data, to improve GRA image quality.

14. The method according to claim 1, wherein the proton beam producing the 9.172 MeV gamma-ray beam at the said $^{13}C(p,\gamma)$ capture resonance has an energy-spread small enough to permit pure nuclear excitation, but may discriminate energetically against events involving concomitant nuclear excitation and ejection of inner-atomic-shell electrons.

15. The method according to claim 14, wherein said ultra-high-resolution proton beam may permit GRA screening with one or more of: a) enhanced detector efficiency due to possibility of using non-resonant-response detector with undiminished contrast sensitivity; b) higher spatial resolution; and c) improved sheet-explosives detection capability.

16. The method according to claim 1, wherein screening the object with the gamma-ray beam from said source is carried out in conjunction with another inspection system, either as part of a multi-tiered explosives-detection facility, or as a multiple-threat detection facility.

17. The method according to claim 16, wherein said other inspection system comprises at least one of a Bremsstrahlung-based system, a radiography system, a tomography system, a fast-neutron-based imaging system, a metal or magnetic-materials detection system, or a vapor-based trace-detection system.

18. The method according to claim 1, wherein performing the scans in at least some of said segments to establish presence of explosives is carried out in addition to scanning for explosives with a dual-E radiography system, that is either bremsstrahlung-based or nuclear reaction-based, and is designed to detect special nuclear materials (SNM).

19. The method according to claim 18, further comprising a dual-purpose ion accelerator, capable of accelerating mixed or alternately-produced protons, $d^+$, and $H_2^+$ beams of intensities of about 0.5-5.0 mA to the same energy/nucleon as the $^{13}C(p,\gamma)$ capture resonance at approximately 1.75 MeV.

* * * * *